United States Patent [19]
Christy

[11] Patent Number: 5,823,969
[45] Date of Patent: Oct. 20, 1998

[54] TACTILE SENSORY TESTING INSTRUMENT

[76] Inventor: George M. Christy, 2108 Raven Rd., Pleasanton, Calif. 94566

[21] Appl. No.: 671,181

[22] Filed: Jun. 27, 1996

[51] Int. Cl.$^6$ .................................................. A61B 19/00
[52] U.S. Cl. .......................................... 600/557; 600/587
[58] Field of Search .............................. 128/738, 740–2, 128/744, 782

[56] References Cited

U.S. PATENT DOCUMENTS

| | | | |
|---|---|---|---|
| 3,185,146 | 5/1965 | Leopoldi | 128/740 |
| 5,381,806 | 1/1995 | Weinstein et al. | 128/744 |

*Primary Examiner*—Max Hindenburg
*Assistant Examiner*—Pamela L. Wingood
*Attorney, Agent, or Firm*—Philip D. Junkins

[57] ABSTRACT

A hand held instrument for use by a health care examiner in test evaluation of the threshold of cutaneous sensory perception of a body surface area of a human patient, particularly the hands and fingers and the feet and toes of the patient. The instrument includes a handle of approximate pencil length and configuration with a pivotal forward head portion. A monofilament element of selected bending force rating is affixed to and projects from the forward head portion of the instrument for application to a body surface area for evaluating the patient's sensory perception thereof. The pivotal forward head portion of the instrument is positionable between two points of filament orientation. The first position of the head portion of the instrument results in projection of the monofilament element in a test evaluation position whereat the filament element extends downwardly from the handle at an angle of about 90 degrees. The second position of the head portion of the instrument results in projection of the monofilament element in a non-test position with the filament element extending in a protected position along the length of the handle.

5 Claims, 1 Drawing Sheet

TACTILE SENSORY TESTING INSTRUMENT

FIELD OF THE INVENTION

The present invention relates generally to devices designed to test for peripheral nerve sensory function. More particularly, the invention relates to devices for testing for peripheral nerve sensory function of the body surface areas of a patient using monofilaments.

BACKGROUND OF THE INVENTION

Monofilament testing for peripheral nerve sensory function has been used has been used more frequently and with renewed interest as the need for screening and monitoring of peripheral nerve function has increased with respect to body therapy. In recent years it has been shown that filaments are a sensitive monitor means for the testing of the peripheral nerve function of a patient, particularly hand and feet body areas. In the 1800's the focus of peripheral nerve testing of the hands was on the study of normal physiology and horsehairs were used as filaments to measure only light thresholds of touch recognition.

In the late 1950's it was determined that a broader range of filament forces were needed than those available with horsehairs to refine the filament method for peripheral nerve testing. Thus, J. Semmes and S. Weinstein designed and developed nylon monofilaments of increasing diameter for peripheral nerve testing with such filaments set at right angles proximate the end of acrylic (Lucite) rods. Such rods, or filament handles, being of approximate pencil length for holding and manipulation by the hand of a therapist or health care examiner measuring the peripheral nerve function of the fingers of a patient.

The Semmes-Weinstein (S-W) monofilament testing devices have become the standard means for repeatable testing and measurement of the threshold of cutaneous sensory perception. Through the 20 unit series of test devices a trained hand therapist or health care examiner can distinguish in a patient between: light touch, diminished light touch, diminished protective sensation, loss of protective sensation, and deep pressure sensation. The series of nylon monofilaments (of uniform 38 mm length) are sized and numbered to correspond to Log (10×force in mg) of force. Lowest force in the series is 4 mg and the highest force is 447 grams. The monofilaments (of constant length, but of increasing diameters) are designed to bend when a specific value of force is reached and such design provides unique control of, and creditability to, the S-W sensory test method. Thus, the series of S-W test devices provides an accurate method by which both diminishing and returning sensation of a patient's body surfaces and extremities can be evaluated and allows the health care examiner to predict and interpret the patient's levels of nerve function and sensibility.

The well known S-W monofilament test units are marketed as a full 20 unit series or as a set of 5 units having selected sensory level designations of 2.83, 3.61, 4.31, 4.56 and 6.65. Although the S-W monofilament test devices are most satisfactory as therapist and health care examiner instruments to evaluate sensory levels of body areas and extremities of patients they are bulky to store, carry and manipulate.

It is a principal object of the present invention to provide improved monofilament instruments for the evaluation of the threshold of cutaneous sensory perception of a patient's body areas and extremities wherein such instruments are of convenient shape when not in use with the monofilament elements protected from undesired bending or buckling forces.

It is a further object of the invention to provide improved hand held monofilament instruments for the screening and monitoring of peripheral nerve function of a patient's extremities (fingers and toes) wherein such instruments include an elongated handle and forward pivot head bearing the monofilament test element.

It is a still further object of the invention to provide improved hand held monofilament peripheral nerve function test instruments which include an elongated handle and a two-position forward pivot head bearing the monofilament test element which is snap-set positionable to orient the monofilament element to a downwardly vertical test position at 90 degrees to the horizontal line of the instrument handle and alternatively to a protected position within the handle.

It is another object of the invention to provide improved hand held monofilament instruments for the evaluation of the threshold of cutaneous sensory perception of a patient's extremities (particularly fingers and hands and toes and feet) wherein such instruments include an elongated handle with a two-position forward pivot head bearing the monofilament test element with the pivot head being snap-set positionable to place the monofilament element in a downwardly vertical test position at right angle orientation with respect to the handle and alternatively to place the monofilament element in a position within the handle whereby the filament element is protected from undesired bending and buckling forces during periods of non-use of the instruments.

Other objects and advantages of the invention will be apparent from the following summary and detailed descriptions of the invention, taken together with the accompanying drawing figures.

SUMMARY OF THE INVENTION

The present invention relates to improved hand held instruments for testing for peripheral nerve sensory function of a patient's body surface areas and extremities, particularly the patient's fingers and hands and toes and feet, using monofilaments of known length, diameter and bending or buckling force rating. The improved instruments of the invention are comprised of a molded plastic handle of approximately pencil length which have attached to their forward end a two-position pivot head bearing a monofilament test element. The pivot head is rotatably attached to the forward (test) end of the instrument handle by forwardly extending handle shank portions which straddle the pivot head.

Each of the shank portions of the instrument handle include two notches for mating with stop projections of the pivot head whereby the monofilament element may be oriented to a vertical downwardly projecting test position or alternatively to a protected position within a bottom channel of the handle when the test instrument is not in use. The handle shank notches and pivot head stop projections are of design and magnitude such that the pivot head must be snap-set to its alternative positions with respect to the handle with the pivot head being held tightly in each position with respect to the handle.

With the pivot head positioned so that the mono-filament element is oriented within the protective handle channel, the instrument of the present invention is of substantially reduced size with respect to the classic Semmes-Weinstein monofilament testing devices and therefore storage and handling of a complete set of the instruments is facilitated and the filaments of the instruments are completely protected. Further, the handle portion of the instruments of the invention may be provided with a pocket clip whereby the therapists and-health care examiners using the instruments may conveniently pocket-carry a selected set of the instruments.

The handles and pivot heads of the instruments of the invention are also provided with pad areas whereby appropriate force rating information of each unit of a series of instruments and marketing source information may be printed.

BRIEF DESCRIPTION OF THE DRAWING FIGURES

Figure 2:
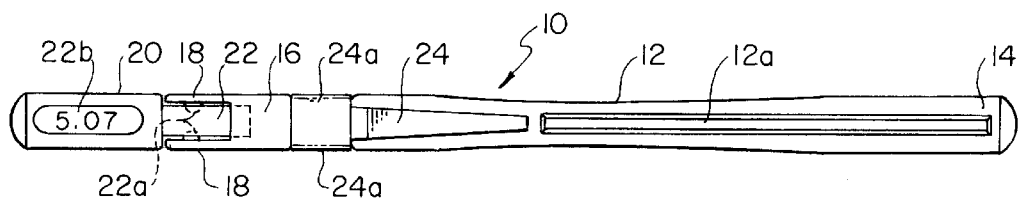
FIG. 2 is a top plan view of the hand held monofilament tactile sensory testing instrument of the present invention.
Figure 4:
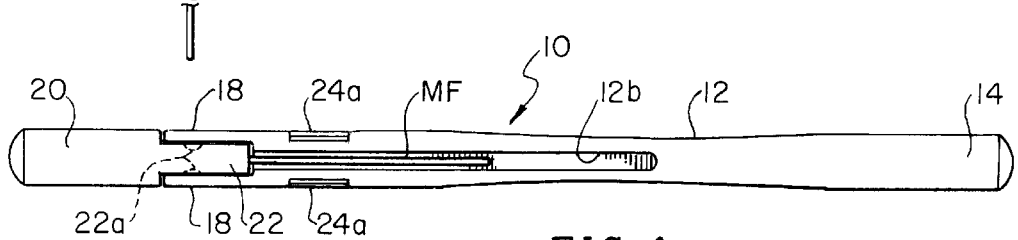
Figure 5:
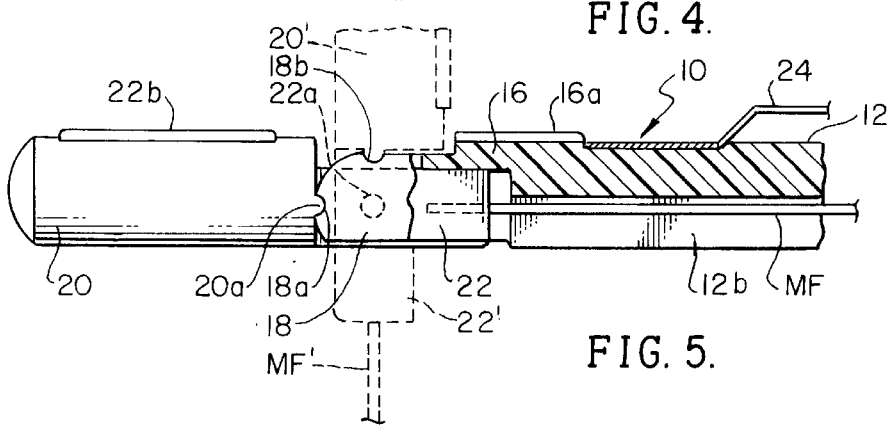

FIG. 4 is a bottom plan view of the testing instrument of FIG. 2 with its forward pivot head snapped into its closed non-test position with the monofilament seated in a protective channel at the underside of the instrument handle; and FIG. 5 is an enlarged partial side view of the forward end of the handle with the pivot head of the instrument of FIG. 2 with the instrument handle shown sectioned and with the pivot head of the instrument shown snapped into its closed non-test position.

DETAILED DESCRIPTION OF A PREFERRED EMBODIMENT OF THE INVENTION

Figure 1:
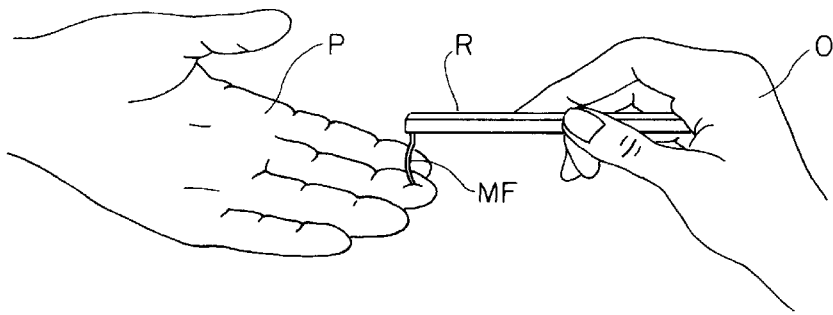
FIG. 1 is a front elevation view of the prior art Semmes-Weinstein hand held monofilament instrument for testing the fingers of a patient for peripheral nerve sensory function.

Referring initially to FIG. 1 there is shown as a front elevation view the prior art Semmes-Weinstein (S-W) hand held monofilament instrument for testing the fingers of a patient "P" for peripheral nerve sensory function. The S-W instrument is held in the hand "O" of the test operator, a hand therapist. The instrument is comprised of a molded acrylic plastic rod R with a nylon monofilament MF depending downwardly from the forward end of the rod at right angle orientation therefrom.

The S-W system of monofilament testing for peripheral nerve sensory function is conducted with a series of the S-W instruments each having a monofilament element of uniform 38 mm length (measured from the rod) and sized and numbered to correspond to Log (10×force in mg) of force. The monofilament elements (of increasing diameter) are designed to bend or buckle when the rated force is reached in downward application of the instrument. With the patient indicating when the filament tip is sensed by one of the series of instruments, the examiner is able to determine a sensory rating for the finger test area of the patient.

Figure 3:
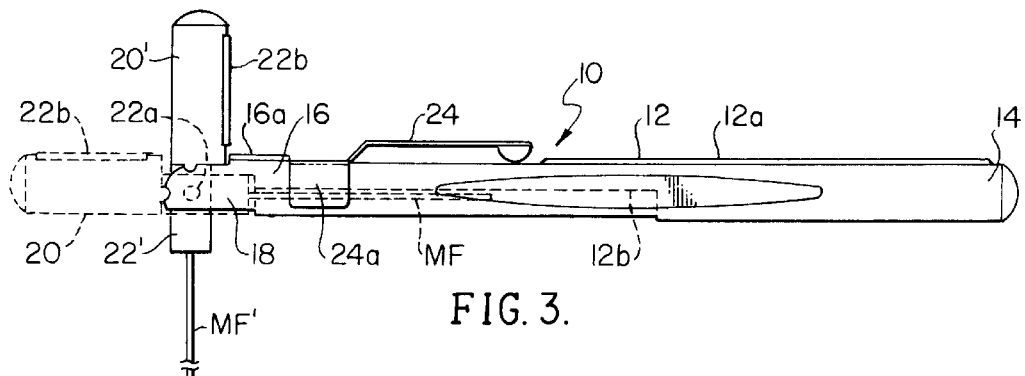
FIG. 3 is a front side elevation view of the tactile sensory testing instrument of FIG. 2 with the forward pivot head of the instrument snapped into its test position with the monofilament of the instrument depending vertically downward with respect to the instrument handle, the pivot head and its monofilament also being shown by dashed outline in its closed position.

Referring now to FIGS. 2, 3 and 4 of the drawing sheet, there is illustrated in a top plan view, a front side elevation view, and a bottom plan view, respectively, the tactile sensory testing instrument 10 of the present invention. The instrument 10 is comprised of a molded plastic handle 12 having a rearward end 14 and a forward end 16. The forward end 16 of the handle 12 includes two integrally molded, forwardly extending handle shank portions 18. The shank portions 18 of the handle 12 extend forwardly in parallel orientation and straddle the rotatable, two-position pivot head 20 of the instrument in its pivot arm portion 22. The pivot arm portion 22 of the pivot head 20 is maintained in its rotatable position between the handle shank portions 18 via recessed pivot spheres 22a which are located between pivot arm portion 22 (on each side thereof) and the straddling shank portions 18 of the handle 12. Alternatively, the pivot spheres may be replaced by a pivot pin extending through the pivot arm portion 22 from the straddling shank portions 18 of the handle 12. A monofilament element MF of appropriate length and diameter is affixed to and extends from the pivot arm portion 22 of the pivot head 20 with the axis of the element MF in alignment with the long axis of the pivot head (see particularly FIG. 4).

As shown in FIGS. 2 and 4, the pivot head 20 is rotated to its non-operative position (non-test position) with the monofilament element MF positioned within protective handle groove 12b located on the underside of the handle 12 (see particularly FIG. 4). FIG. 5 is an enlarged partial side view of the forward end of the instrument handle 12 with the pivot head 20 of the instrument 10 snapped into its closed non-test position and with the monofilament element MF positioned within handle groove 12b. The pivot head 20 is held in the non-operative position by pivot head stop projections 20a which are located on each side of the pivot head and which are snap-seated into notches 18a located at the terminal end surface of the straddling shank portions 18 of the handle 12. The operative position of the pivot head 20 is shown in FIG. 5 in dashed outline as pivot head 20' with the pivot head stop projections 20a snap-seated into notches 18b located at the upper and rearward terminus of the arcuate surface of the straddling shank portions 18 of the handle 12. In the operative position (dashed outline), the pivot arm portion 22' of the pivot head 20' is shown depending downwardly from the instrument handle 12 whereby the monofilament test element MF', carried by the pivot arm portion 22', is oriented downwardly at an angle of 90 degrees with respect to the handle 12 and is rigidly fixed (snap-set) in such position for use in evaluating the threshold of cutaneous sensory perception of a patient's fingers and hands.

The operative position of the pivot head 20' is also shown in FIG. 3 with the entire handle portion 12 of the test instrument. In such figure the non-operative position of the pivot head with respect to the instrument handle 12 is shown in dashed outline as pivot head member 20 with the monofilament element MF being protectively seated within the channel 12b of the handle.

As shown in FIGS. 2 and 3, the handle portion 12 of the instrument 10 of the invention may include an elongated raised platform or plateau surface area 12a upon which may be printed or etched marketing source or other appropriate information. The pivot head 20 of the instrument may also include a platform or plateau surface area 22b upon which (as particularly shown in FIG. 2) may be printed appropriate information identifying the force rating of the monofilament element affixed to the pivot head. Further, the handle portions 12 of the instruments 10 of the invention may be provided with a pocket clip 24 whereby the hand therapists using the instruments may conveniently pocket-carry a selected set of the instruments. The pocket clip 24 may be of well known structure including a grip position 24a which snap-affixes the clip to the instrument handle 12.

It is to be understood that, although the test instrument of the present invention has been described with respect to its use by a health care examiner for the evaluation of the threshold of cutaneous sensory perception of a patient's extremities (particularly the patient's fingers and hands and toes and feet), the tactile sensory testing instrument of the invention may be utilized for the evaluation of the threshold sensory perception of all skin surface areas of a human patient. Further, while the invention has been described in connection with a particular structural embodiment of the tactile sensory testing instrument, modifications of the basic two-position monofilament element shift means for the instrument may become apparent to those skilled in the sensory testing art. Accordingly, such modifications are to be included within the spirit and scope of the invention as defined in the following claims.

What I claim is:

1. A hand held instrument for use by a health care examiner in test evaluation of the threshold of cutaneous sensory perception of a body surface of a human patient comprised of:
    a) an instrument handle having a forward end and a rearward end, said handle provided with an elongated channel along its lower surface;
    b) a pivot head member having a forward end and a rearward end, said head member being rotatably affixed proximate its rearward end to the forward end of said handle for rotational positioning of said head member alternatively between a test evaluation position and a non-test position; and
    c) a monofilament element of selected standard length and bending force rating affixed to and projecting from the rearward end of said pivot head member for application to a body surface area of a patient for evaluating the sensory perception thereof,
        said pivot head member and the forward end of said instrument handle having cooperative means for positioning said head member with its projecting monofilament in said test evaluation position whereby said monofilament element extends downwardly from said handle at an angle of about 90 degrees therefrom and for alternatively positioning said head member with its projecting monofilament in said non-test position with said monofilament element extending in a filament protected position along the length of said handle within said elongated channel.

2. A hand held instrument for use by a health care examiner in test evaluation of the threshold of cutaneous sensory perception of a surface of a human patient as claimed in claim 1 wherein the cooperative means for rotationally positioning said head member with respect to the instrument handle is comprised of a stop projection on each side of said head member for snap-set mating alternatively with two pairs of notches at the forward end of said handle, said two pairs of notches being spaced apart by about 90 rotational degrees whereby when said stop projections are snap-set into one of said pairs of notches the monofilament element of said head member extends downwardly from said handle at an angle of about 90 degrees therefrom to said test evaluation position and when said stop projections are snap-set into the other of said pairs of notches the monofilament element of said head member extends in a filament protected position within said elongated channel along the length of said handle.

3. A hand held instrument for use by a health care examiner in test evaluation of the threshold of cutaneous sensory perception of a body surface area of a human patient as claimed in claim 1 wherein the forward end of said handle includes two forwardly extending handle shank portions which straddle the rearward end of said pivot head member and maintain said head member in its rotational orientation at the forward end of said handle, said head member and said handle shank portions having said cooperative means for positioning said head member in its test position and alternatively positioning said head member in its non-test position.

4. A hand held instrument for use by a health care examiner in test evaluation of the threshold of cutaneous sensory perception of a body surface area of a human patient as claimed in claim 1 wherein said instrument handle and said pivot head member are fabricated of a molded plastic material and said monofilament element is formed of a natural or synthetic fiber filament having an selected standard length from its tip to said handle of 38 mm.

5. A hand held instrument for use by a health care examiner in test evaluation of the threshold of cutaneous sensory perception of a patient's extremities, including the patient's hands, fingers, feet and toes, comprised of:
    a) a molded plastic instrument handle having a forward end and a rearward end, said handle provided with an elongated channel along its lower surface and said handle in its forward end including two forwardly extending parallel handle shank portions with each shank portion having a forward notch and an upper notch spaced apart by about 90 rotational degrees;
    b) a pivot head member having a forward end and a rearward end, said head member being rotatably affixed proximate its rearward end to the forward end of said handle between said parallel shank portions for rotational positioning of said head member alternatively between a test evaluation position and a non-test position, said pivot head member including a stop projection on each side thereof for snap-set mating alternatively with the forward notch and upper notch of the said parallel handle shank portions; and
    c) a monofilament element of selected standard length and bending force rating affixed to and projecting from the rearward end of said pivot head member for application to a patient's extremities for evaluation of the sensory perception thereof,
        said pivot head member and said monofilament element being rotationally positionable with respect to the instrument test orientation with said monofilament element extending downwardly from said handle at an angle of about 90 degrees therefrom when the said stop projections of said pivot head member are snap-set into the upper notches of said handle shank portions, and said pivot head member and said monofilament element being rotationally positionable with said monofilament extending in a protected non-test position along the length of said handle within said elongated channel when the said stop projections of said pivot head member are snap-set into the forward notches of said handle shank portions.

* * * * *